United States Patent [19]

Moyer et al.

[11] Patent Number: 4,503,393

[45] Date of Patent: Mar. 5, 1985

[54] METHOD AND APPARATUS FOR DETECTING FLAWS IN THE THREADED END OF AN ELONGATE MEMBER USING ELECTROMAGNETIC EXCITATION AND AN AUTOMATED SCANNING SENSOR

[75] Inventors: Mark C. Moyer; Clifford W. Petersen, both of Missouri City; Felix N. Kusenberger, San Antonio; William D. Perry, San Antonio; Floyd A. Balter, San Antonio; Cecil M. Teller, II, San Antonio, all of Tex.

[73] Assignee: Exxon Production Research Co., Houston, Tex.

[21] Appl. No.: 308,749

[22] Filed: Oct. 5, 1981

[51] Int. Cl.³ .................... G01N 27/72; G01R 33/12
[52] U.S. Cl. .................................. 324/235; 324/220; 324/238; 324/262
[58] Field of Search ............................... 324/219–221, 324/227, 228, 235, 238–243, 251, 262; 74/22 R, 84 D

[56] References Cited

U.S. PATENT DOCUMENTS

| 2,582,437 | 1/1952 | Jezewski et al. | 324/241 |
|---|---|---|---|
| 2,965,840 | 12/1960 | Renken, Jr. et al. | 324/232 |
| 2,983,141 | 5/1961 | Vanator | 324/207 |
| 3,327,205 | 6/1967 | Wood et al. | 324/220 |
| 3,437,917 | 4/1969 | Gunkel et al. | 324/240 X |
| 3,496,457 | 2/1970 | Proctor et al. | 324/225 |
| 3,539,006 | 11/1970 | Hanna | 324/238 |
| 3,710,236 | 1/1973 | Halsey et al. | 324/235 |
| 4,002,966 | 1/1977 | Hinds et al. | 324/238 |
| 4,105,972 | 8/1978 | Smith | 324/238 |
| 4,188,577 | 6/1980 | Mhatre et al. | 324/238 |
| 4,281,230 | 7/1981 | Naylor | 200/61.58 R |

FOREIGN PATENT DOCUMENTS

| 102020.7 | 8/1980 | European Pat. Off. . |
|---|---|---|
| 0039793 | 11/1981 | European Pat. Off. . |
| 0065325 | 11/1982 | European Pat. Off. . |
| 1471595 | 4/1977 | United Kingdom . |
| 1498218 | 1/1978 | United Kingdom . |
| 1539313 | 1/1979 | United Kingdom . |
| 2012966 | 8/1979 | United Kingdom . |
| 1562631 | 3/1980 | United Kingdom . |
| 2071331 | 9/1981 | United Kingdom . |
| 1604188 | 12/1981 | United Kingdom . |

Primary Examiner—Gerard R. Strecker
Assistant Examiner—Walter E. Snow
Attorney, Agent, or Firm—Marc L. Delflache

[57] ABSTRACT

Apparatus for detecting flaws in the threaded end of a ferromagnetic pipe is disclosed. The apparatus comprises means for applying a magnetic force to produce a field generally axially through the threaded end of the pipe, first and second means adjacent successive crests of a thread for sensing a generally radial magnetic field and generating a first and second signal corresponding to the sensed magnetic fields, and means for differentially connecting the signals generated by said first and second sensing means, whereby a differential output signal is produced in response to a flaw between the crests of the thread being inspected. The apparatus also comprises means for helically rotating said sensing means to follow a path corresponding to the threads of the pipe, whereby the first and second signals vary with time.

A method for detecting flaws in the threaded end of a ferromagnetic pipe is also disclosed. The method comprises the steps of applying a magnetic force to produce a field generally axially through the threaded end of the pipe, sensing the radial magnetic field adjacent successive crests of a thread of the pipe, generating first and second signals corresponding to the sensed magnetic fields, and differentially connecting the first and second signals.

26 Claims, 9 Drawing Figures

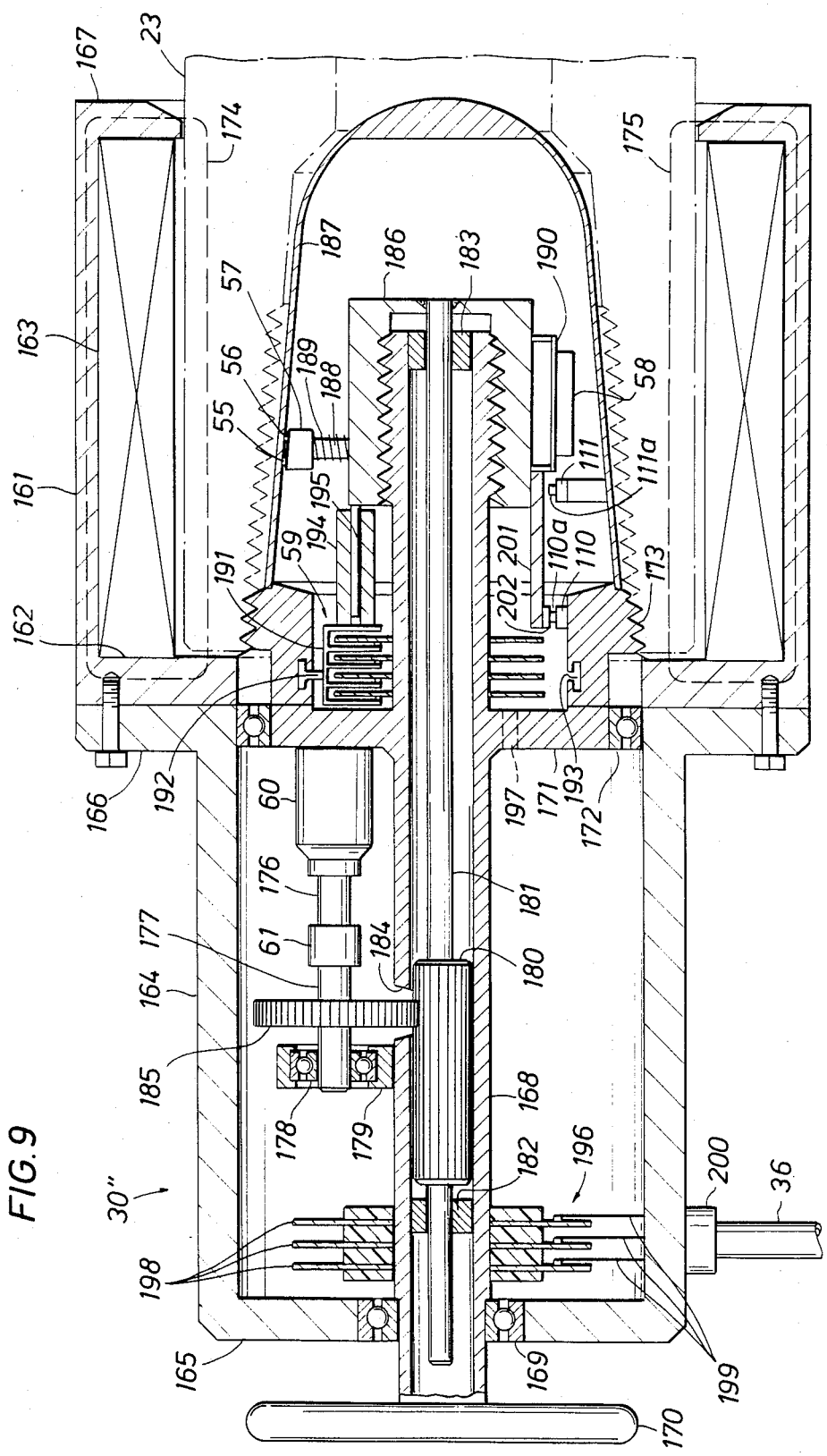

METHOD AND APPARATUS FOR DETECTING FLAWS IN THE THREADED END OF AN ELONGATE MEMBER USING ELECTROMAGNETIC EXCITATION AND AN AUTOMATED SCANNING SENSOR

FIELD OF THE INVENTION

This invention relates to detecting flaws in the threaded end of a pipe, and more particularly to a method and apparatus therefor.

BACKGROUND OF THE INVENTION

The steadily increasing demand for energy in the form of gas and oil has required the drilling of wells at ever-increasing depths. The loss of a rotary bit, drill collar, or the lower portion of a drill string in these wells is very costly ("The Importance of Quality Tubular Inspections" by M. C. Moyer, et al., Oil & Gas Journal, Apr. 13, 1981). Because flaws occur in drill pipes and collars as a result of tensile, compressive, torsional and bending stresses encountered during the drilling operation, it is not uncommon for each length of drill pipe and each drill collar to be inspected prior to use in drilling a new well. Currently, the magnetic particle method is used for the inspection of drill pipe and collars. While experience has shown results obtained using the magnetic particle method are generally better than most, increased flaw-detection sensitivity is necessary, particularly in the threaded regions of tool joints, if costly failures are to be significantly reduced.

Referring more specifically to FIG. 1, a tool joint, indicated generally at 20, comprises a pin 21 of one drill pipe 22 threadably engaged within the box 23 of a second drill pipe 24 so that the end of the box 23 butts against the shoulder 25 of the pin 21. A thread indicated generally at 26 comprises a helical root 27 bordered by crests 28 and 29. Flaws in the threads of the tool joint 20 tend to occur in the last engaged threads of the pin 21 near the shoulder 25 or the last threads of the box 23 outside the engaged region. When the tool joint is new, failures occur primarily in the threads of the pin 21 rather than the threads of the box 23 because of the preloaded stress distribution and the presence of initiating sources such as tool marks, nicks, gouges, corrosion, etc. However, as the tool joint 20 is used in service, failures occur more frequently in the threads of the box 23 because of the wear on the outside diameter. Consequently, the threads of both the pin 21 and the box 23 must be inspected. Since the inspection activities must be conducted primarily at the drill site, adequate consideration must be given to the undesirable environment and operational conditions at the drill site.

As mentioned above, the magnetic particle method is used for the inspection of the threads of box and pin joint regions. This has been accomplished by magnetizing the region or providing it with a residual magnetic field and thereafter dusting fine particles of iron or iron oxides on the region to ascertain whether or not there are any defects of the type referred to above. However, this type of inspection has serious limitations inasmuch as the threads must first be cleansed of any oil, dirt, corrosion, or the like. Additionally, the inspection is very dependent on the visual acuity of the inspector.

U.S. Pat. No. 3,327,205 granted June 1967 to F. M. Wood, et al., discloses apparatus for inspecting the threaded ends of pipe which comprises a housing for securing the outer diameter of the pipe being inspected, a rotor adapted for circumferential rotation with respect to the central axis of the pipe, a search shoe moved longitudinally by the rotor with respect to the pipe and having a threaded portion for engagement with the threads of the pipe to be inspected. Means are mounted in the threaded portion of the shoe for sensing a transverse magnetic field. Consequently, the magnetic responsive means must be positioned in very close proximity to the root of the pipe thread on which the shoe rides. Although the accuracy of this apparatus surpasses that of the magnetic particle method, it still requires that the threads be cleansed so that the magnetic responsive means ride in very close proximity to the root of the pipe threads. Also, no mention is made of the magnetization field required to accurately identify flaws via the magnetic responsive means.

SUMMARY OF THE INVENTION

The instant invention is based on the discovery of a method and apparatus for detecting flaws in the threaded end of a ferromagnetic pipe. The term "flaw," as used herein, includes any discontinuity or irregularity in the threaded end of the pipe such as for example, fatigue cracks, pin stretch, box swell and the like. The apparatus comprises first and second means adjacent the crests of a thread for sensing a radial magnetic field and generating a first and second signal corresponding to the sensed magnetic fields, and means for differentially connecting the signals generated by said first and second sensing means. The apparatus also comprises means for applying a magnetic force to produce a field generally axially through the threaded end of the pipe by a closed magnetic circuit constructed to minimize the reluctance and the demagnetization due to isolated magnetic poles so that the force is large enough to magnetically saturate the end of the pipe during a first inspection mode. The apparatus further includes means to maintain a residual magnetic force through the threaded end of the pipe by the same magnetic circuit during a second mode of inspection.

Because the sensing means are not positioned in close proximity to the root of the thread like Wood, but rather adjacent the crests of the thread, the sensing means can be mechanically isolated from the threads of the pipe to facilitate testing in a field operation and to eliminate any requirement of cleaning the threads before inspection. Mechanical isolation is accomplished by inserting a nonmagnetic material between the sensing means and the crests of the threads to prevent damage to the former during inspection in a field operation. Additionally, the differential output signal produces a distinct signature identifying the existence of a specific flaw occurring between the crests of the thread being inspected. The art does not suggest a method or apparatus for detecting flaws by specific identification while at the same time mechanically isolating the apparatus from the pipe being inspected.

BRIEF DESCRIPTION OF THE DRAWINGS

FIG. 9 is a partially schematic, vertical sectional view of a magnetizing head of the system shown in FIG. 3 to inspect the box of the tool joint of FIG. 1 in accordance with the invention.

DETAILED DESCRIPTION OF THE INVENTION

Figure 1:
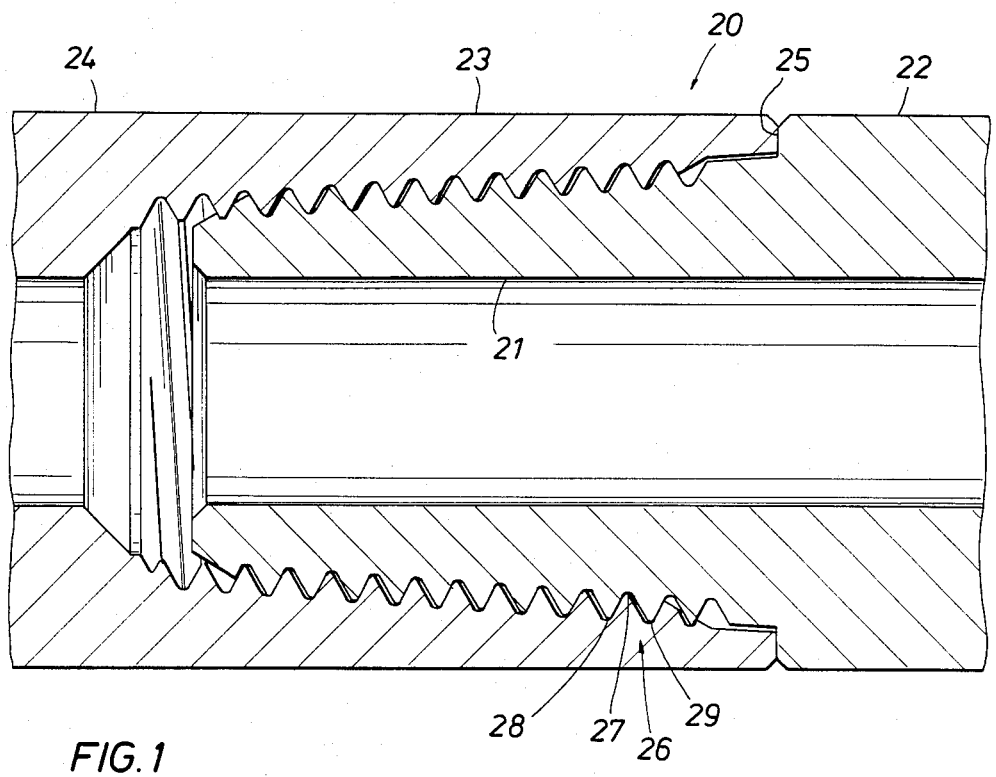
FIG. 1 is a vertical sectional view of a tool joint.
Figure 2:
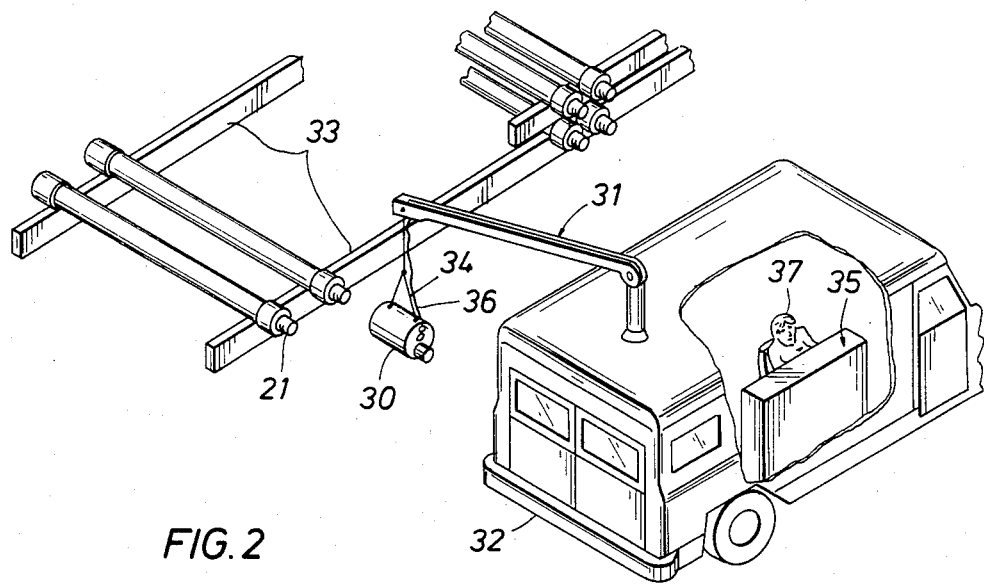
FIG. 2 is a perspective view of the inspection system in accordance with the invention.

Referring now in more detail to FIG. 2, an inspection head 30 is positioned by a boom 31, which is supported on a truck 32 or other mechanical lifting structure to internalize the pin 21 of the pipe 22, lying on a rack 33 at a remote field site. The head 30 is mechanically connected to the boom 31 by a wire yoke 34 and electrically connected to electronic equipment 35 in the truck 32 by a cable 36 which runs up the yoke 33, through the boom 31 and into the truck 32. The electronic equipment 35, operated by a person 37 seated in the truck 32, is powered by a portable generator (not shown) which provides approximately 115 VAC thereto at a terminal 38 shown in FIG. 3. It is to be understood that the inspection head 30 is not limited to a portable configuration, but could also be configured as a fixed station.

The electronic equipment 35 is represented by the elements shown within a dashed line 35 and comprises a magnetizing power supply 39, a control unit 40 and a signal power supply 41, each of which receives 115 VAC through the terminal 38. The equipment 35 further comprises a differential circuit 42 powered by the signal power supply 41, and a strip chart 43 powered through the control unit 40 for receiving the output from the differential circuit 42 at a terminal 44. One function of the control unit 40 is to properly sequence the magnetizing power supply 39. The inspection head 30 is represented by the elements shown within a dashed line 30 and is positioned to internalize the pin 21. The cable 36 (FIG. 2) comprises the nine lines shown in FIG. 3 which run between the head 30 and the equipment 35 through connectors 45 through 53.

The inspection head 30 comprises a magnetizing circuit 54 energized by the magnetizing power supply 39 through the connector 45 for applying a magnetic force generally axially through the pin 21, and two sensing units 55 and 56 positioned adjacent the crests 28 and 29 of the thread 26 for sensing a radial magnetic field and generating signals S1 and S2, respectively, which correspond to the sensed magnetic fields. The sensing units 55 and 56 are mounted on a bracket 57. The head 30 also comprises an amplifier 58 for increasing the amplitude of the signals S1 and S2 and a slip ring assembly 59 for transmitting those signals from the amplifier 58 to the differential circuit 42, through the connectors 51 and 52, respectively. The slip ring assembly 59 also transmits power, P, from the signal power supply 41 through the connector 50 to the sensing units 55 and 56 and the amplifier 58. The head 30 further comprises a motor 60 and a clutch 61, both powered by the control unit 40 through connectors 49 and 48, respectively. The motor 60 drives the clutch 61 as indicated by dotted line 60a, which when enabled by the control unit 40 rotatably engages the bracket 57, as indicated by dotted line 61a, so that the sensing units 55 and 56 follow a helical path corresponding to the threads of the pin 21. Each time the bracket 57 rotates through an angular displacement of approximately 60 degrees, the slip ring assembly 59 provides a momentary contact signal (M) through the connector 53 to the strip chart 43 at a terminal 62. The head 30 finally comprises two limit switches 63 and 64 electrically connected through the connectors 46 and 47, respectively, to the control unit 40. One is enabled when the sensing unit bracket 57 is positioned over the end threads of the pin 21 and the other is enabled when the bracket 57 is positioned over the threads adjacent the shoulder 25 of the pin 21 as represented by the dotted line 57a.

Figure 4:
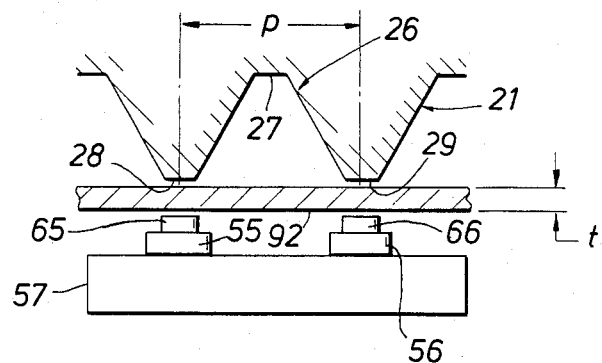
FIG. 4 is a partially schematic, vertical sectional view of means for sensing a magnetic field in accordance with the invention.

Referring in more detail to FIG. 4, the sensing units 55 and 56 mounted on the bracket 57 house Hall elements 65 and 66, respectively, which can be, for example, a type BH-700 manufactured by F. W. Bell. The preferred orientation of the elements with respect to the pin 21 requires that the sensing surface of each element 65 and 66 be aligned on a plane parallel to the flats of the crests 28 and 29 and that the centerlines of the elements 65 and 66 each be aligned over the center of the crests 28 and 29, respectively, so that the distance therebetween is approximately equal to the pitch (p) of the thread 26 of the pin 21. It is to be understood, however, that other means responsive to magnetic flux can be used such as, for example, coils, magnetometers, magnetodiodes, and similar devices.

Figure 5:
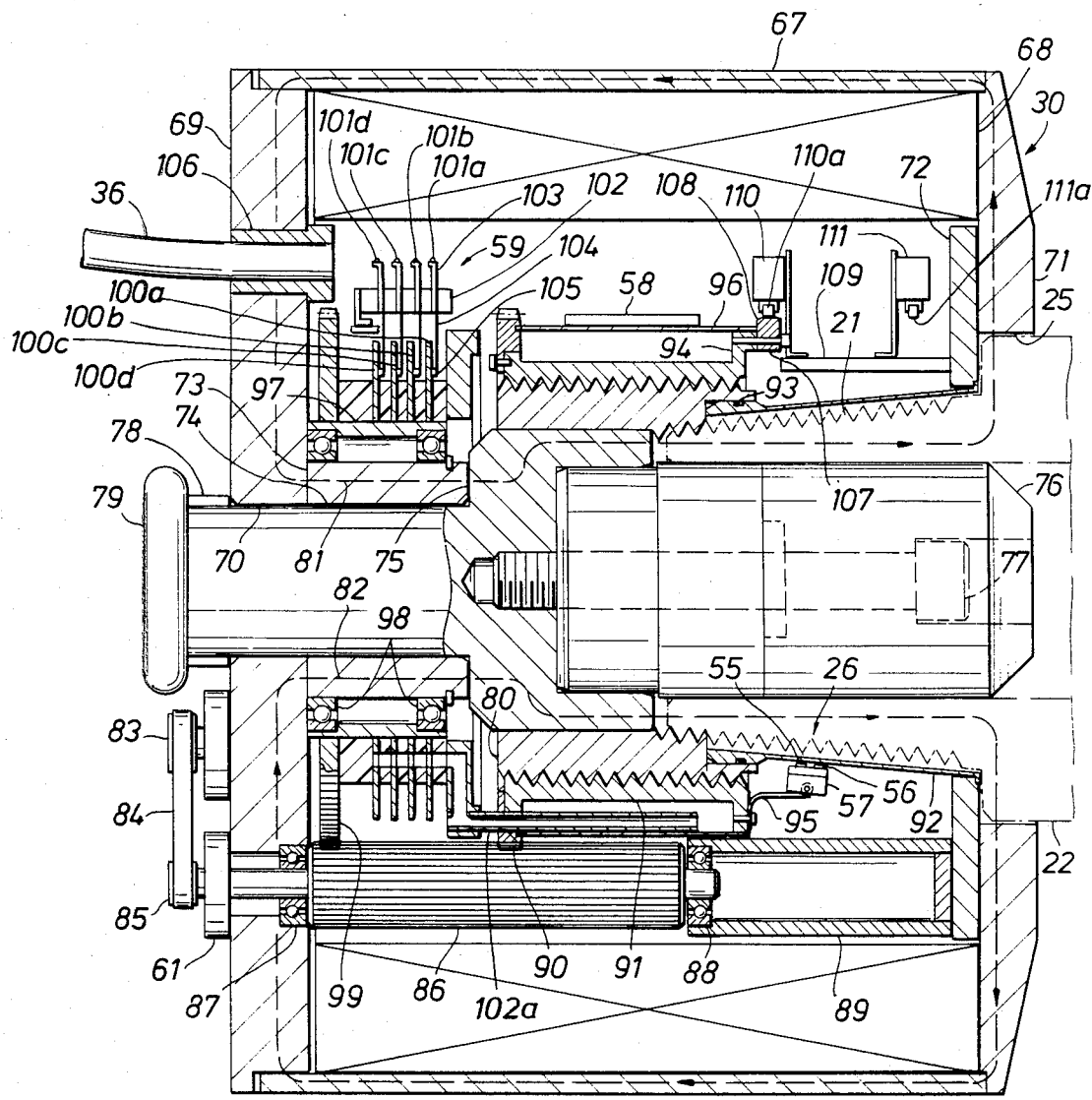
FIG. 5 is a partially schematic, vertical sectional view of a magnetizing head of the system shown in FIG. 3 to inspect the pin of the tool joint in FIG. 1 in accordance with the invention.

Referring in more detail to FIG. 5, a head for inspecting the pin 21 is indicated generally at 30' and represents the embodiment of the head 30 described above with respect to FIG. 3. The head 30' (FIG. 5) comprises a tubular housing 67, a solenoid 68 positioned longitudinally within the housing 67, a plate 69 closing the back end of the housing 67 and having a concentric hole 70 drilled therethrough, an annulus 71 closing the other end of the housing 67 and having an inner diameter sufficiently large to receive the pipe 22, and a retaining annulus 72 attached concentrically to the inside surface of the receiving annulus 71 and having an inside diameter sufficiently large to receive the pin 21 of the pipe 22. The head 30' also comprises a cylindrical sleeve 73 having one end attached to the inside surface of the back plate 69 in concentric alignment with the hole 70 therethrough, a journal 74 rotatably mounted within the sleeve 73 and the hole 70 through the back plate 69, a cup-shaped guide mount 75 having a base attached to one end of the journal 74 and abutting against the other end of the sleeve 73, and a cylindrical guide 76 seated within the cavity of the mount 75 and extending axially therefrom to a chamfered end concentrically positioned within the orifice of the receiving annulus 71. The guide is attached to the mount 75 by a bolt 77 extending longitudinally therethrough. A handle 79 for rotating the journal 74 and the mount 75 is attached to the other end of the journal 74, the axial position of which is fixed by a retainer 78 attached thereto and butting against the outside surface of the back plate 69. A portion of the inside surface of a tubular screw 80 fits over and is attached to the outside surface of the walls of the mount 75, the remaining portion of the inside surface being threaded to engage the end of the pin 21. When the pin 21 of the pipe 22 is inserted into the head 30', it is piloted through the orifice of the receiving annulus 71 by the guide 76 and threadably engaged by the tubular screw 80 as the handle 79 is rotated so that the shoulder 25 of the pin 21 moves toward the retaining annulus 72.

The magnetizing circuit 54 (FIG. 3) comprises all the above-mentioned elements which are ferromagnetic except the handle 79 (FIG. 5), the chamfered end of the guide 76, and the retaining annulus 72 which are fabricated from a nonmagnetic material. The solenoid 68 is connected to the magnetizing power supply 39 (FIG. 2) which supplies up to 15 amperes of direct current at approximately 20 volts to achieve a flux density in air of approximately 300 gauss. When the pin 21 (FIG. 5) is engaged by the tubular screw 80 within the head 30', as described hereinabove, and the solenoid 68 is energized, a magnetic flux is generated through the ferromagnetic elements of the magnetizing circuit 54 and the pin 21 along doughnut-shaped path approximated in cross-section by dashed lines 81 and 82, as well as the magnetic end of the guide 76. (It is to be understood that the invention can also be practiced when the flux flows in a direction opposite that indicated by the dashed line 81 and 82. This is accomplished by reversing the direction of current flow through the solenoid 68.) The path is a magnetic circuit wherein the reluctance and the demagnetization due to isolated magnetic poles has been greatly reduced by concentrating the flux through adjacent ferromagnetic elements which along with the pin 21 form a closed circuit having minimal air gaps therebetween. As a result, the magnetic force or ampere-turns produced by the solenoid 68 to magnetically saturate the pin 21 is greatly reduced. Consequently, the head 30' is small in size and requires less current to achieve saturation, i.e., approximately eight amperes.

The motor 60, which has a peak torque rating of approximately 140 oz-in, and the clutch 61 which can be, for example, an electrical friction type are mounted on the outside surface of the back plate 69. The motor 60 rotates a pulley 83 which turns a belt 48 to drive a pulley 85 mounted on the shaft of the clutch 61. When the clutch 61 is enabled by the control unit 40, it engages the journaled end of an elongated spur gear 86 which extends through the back plate 69 and is rotatably supported therein by a bearing 87. The other end of the spur 86 is journaled on a bearing 88 mounted on a bracket 89 attached to the retaining annulus 72. The spur gear 86 engages a gearwheel 90 mounted on one end of a cylindrical tube 91, the inside surface of which threadably engages the tubular screw 80. A nonmagnetic shell 92 having the shape of a conical frustum, which corresponds to the taper of the pin 21 and the outer diameter of its crests, is attached at its base to the orifice of the retaining annulus 72 and tapers to a ring bushing 93 rotateably mounted and sealed within the inside surface of the tubular screw 80. When the pin 21 of the pipe 22 is inserted into the head 30's to threadably engage the tubular screw 80, the handle 79 is rotated until the thread crests of the pin 21 seat against the inner surface of the conical shell 92. The other end of the cylindrical tube 91 has a rim 94 extending radially outwardly therefrom to support a pair of cantilevered leaf springs 95 extending in a direction tangent to the curvature of the conical shell 92. The bracket 57 for the sensing units 55 and 56 is mounted on the springs 95 so that the sensing units 55 and 56 are also tangent to the conical shell 92 at the point of contact. The torsional compliance of the springs 95 permits the sensing units 55 and 56 to follow the taper of the shell 92. As the tube 91 is rotated on the tubular screw 80 by the gear wheel 90, which slides axially with the tube 91 along the teeth of the spur gear 86 as it is being driven by the motor 60.

The threads of the tubular screw 80 which engage the cylindrical tube 91 have a pitch equal to the horizontal component of the pitch of the pin 21 so that the sensing units 55 and 56 follow the helical path defined by the threads of the pin 21 with the shell 92 disposed therebetween. The position of the sensing units 55 and 56 with respect to the thread 26 is the same as explained hereinabove with respect to FIG. 4. Because the reluctance and demagnetizing effect of the magnetic circuit 54 has been greatly reduced as discussed above, the head 30' is made mechanically more rugged to enhance its reliability when used in the field by inserting the shell 92 between the pin 21 and the Hall elements 65 and 66 with an acceptable amount of signal attenuation. The shell 92 can be, for example, brass, phosphor bronze, beryllium copper or any other nonmagnetic material having a low coefficient of friction with respect to the tubular screw 80, and has a thickness (t) between approximately 0.010 and 0.050 inch. The preferred thickness is approximately 0.015 inch when considering the balance between signal attenuation and mechanical durability. As can be seen, the pin 21 and the outside environment are mechanically isolated from the inside components of the head 30' during inspection even though the pin 21 itself is incorporated into the magnetic circuit 54. Also, since the pin 21 is isolated from the sensing units 55 and 56 and there is no requirement to position the elements 65 and 66 close to the root 27 of the thread 26, the pin 21 can be inspected without cleaning the threads.

Referring back to FIG. 5, the amplifier 58 is mounted on a circuit board 96 which is attached between the gearwheel 90 and the rim 94 of the cylindrical tube 91 and, therefore, rotates on the tube 91 with the sensors 55 and 56. The slip ring assembly, indicated generally at 59 comprises a collar 97 rotatably mounted by bearings 98 on the sleeve 73, a gearwheel 99 mounted on the collar 97 and rotatably engaging the spur gear 86, successive slip rings 100a through 100d concentrically aligned and mounted on the collar 97, and successive brush assemblies 101a through 101d mounted on a bracket 102 attached to the back plate 69 and in slidable electric contact with the slip rings 100a through 100i d, respectively. Thus, the rotation of the slip rings 100a through 100d is synchronized with that of the amplifier 58 through the gearwheels 99 and 90, respectively. Because rotation is synchronized, the slip rings 100a through 100d are electrically connected to the amplifier 58 through a conduit 102a which provides a pathway through the gearwheel 90 and each of the slip rings 100a through 100d as the gearwheel 90 moves axially along the teeth of the spur gear 86. Although only four slip rings 100a through 100d are illustrated, an additional four 100e through 100h (not shown) are used in operation along with corresponding brush assemblies 101e through 101h. Referring only to one brush assembly 101a, each of the brush assemblies 101a through 101d comprises a terminal 103 mounted on the bracket 102, an electrically conductive leaf spring 104 having one end electrically and mechanically attached to the terminal 103, and a brush 105 mounted on the other end of the leaf spring 104 which holds the brush 105 in slidable electric contact with the corresponding slip ring 100a. The terminal 103 of each brush assembly 101a through 101d is electrically connected to a corresponding wire extending through a grommet 106 in the back plate 69 as part of the cable 36.

The rim 94 of the cylindrical tube 91 also supports an arm 107 extending axially therefrom toward the retaining annulus 72 and carrying a cam 108. A bracket assembly 109 attached to the retaining annulus 72 supports a NEAR limit switch 110 and a FAR limit switch 111, each of which can be actuated by the cam 108. When the motor 60 starts rotating the cylindrical tube 91, the cam 108 rotates away from and releases the actuating roller 110a of the NEAR limit switch 110. After the cylindrical tube 91 has rotated to the end of the helical path, the cam 108 rotates under the roller 111a of the FAR limit switch 111 which is actuated thereby. Both of the switches 110 and 111 and the solenoid 68 also are electrically connected to wires extending through the grommet 106.

Figure 3:
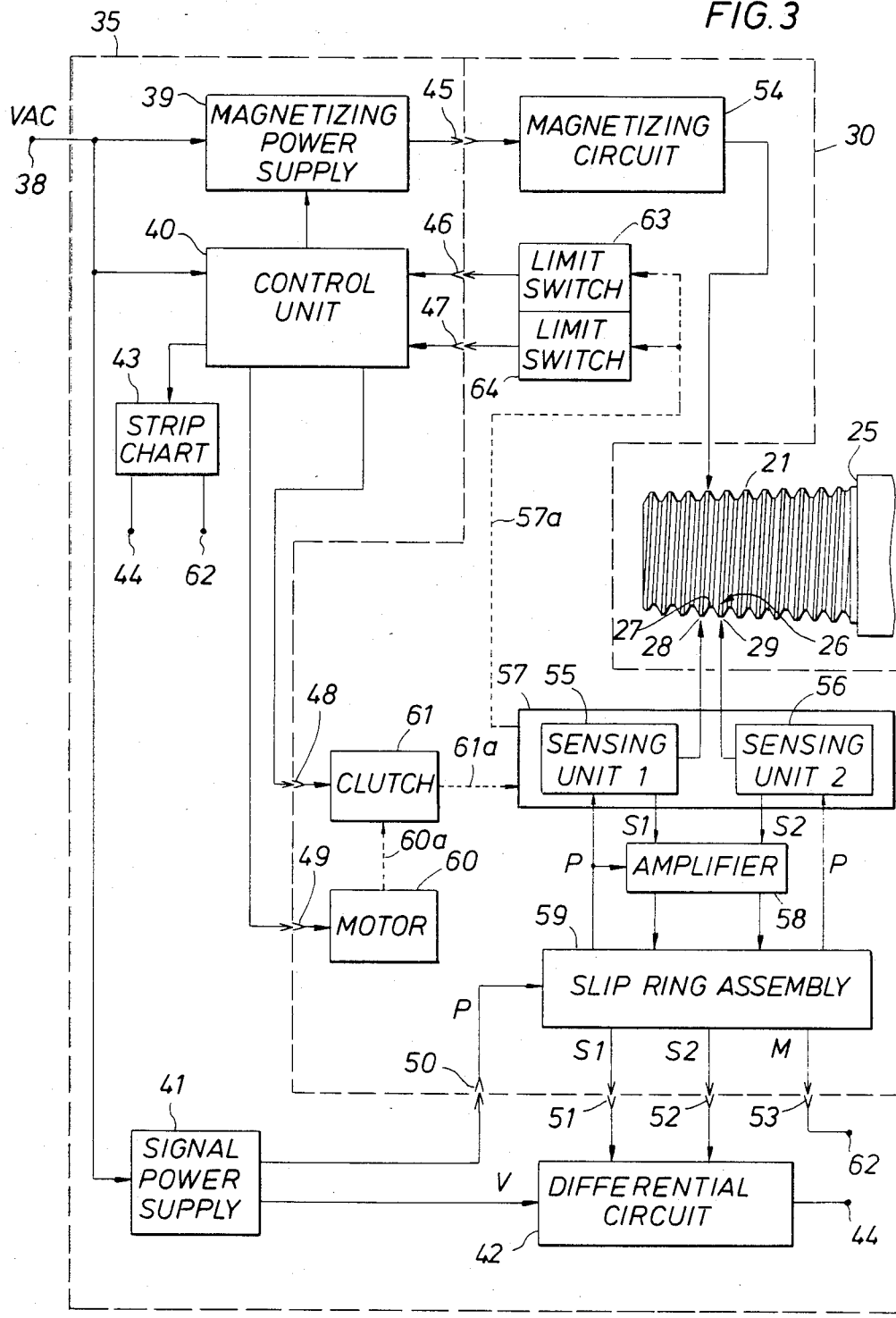
FIG. 3 is a block diagram of the inspection system in accordance with the invention.
Figure 6:
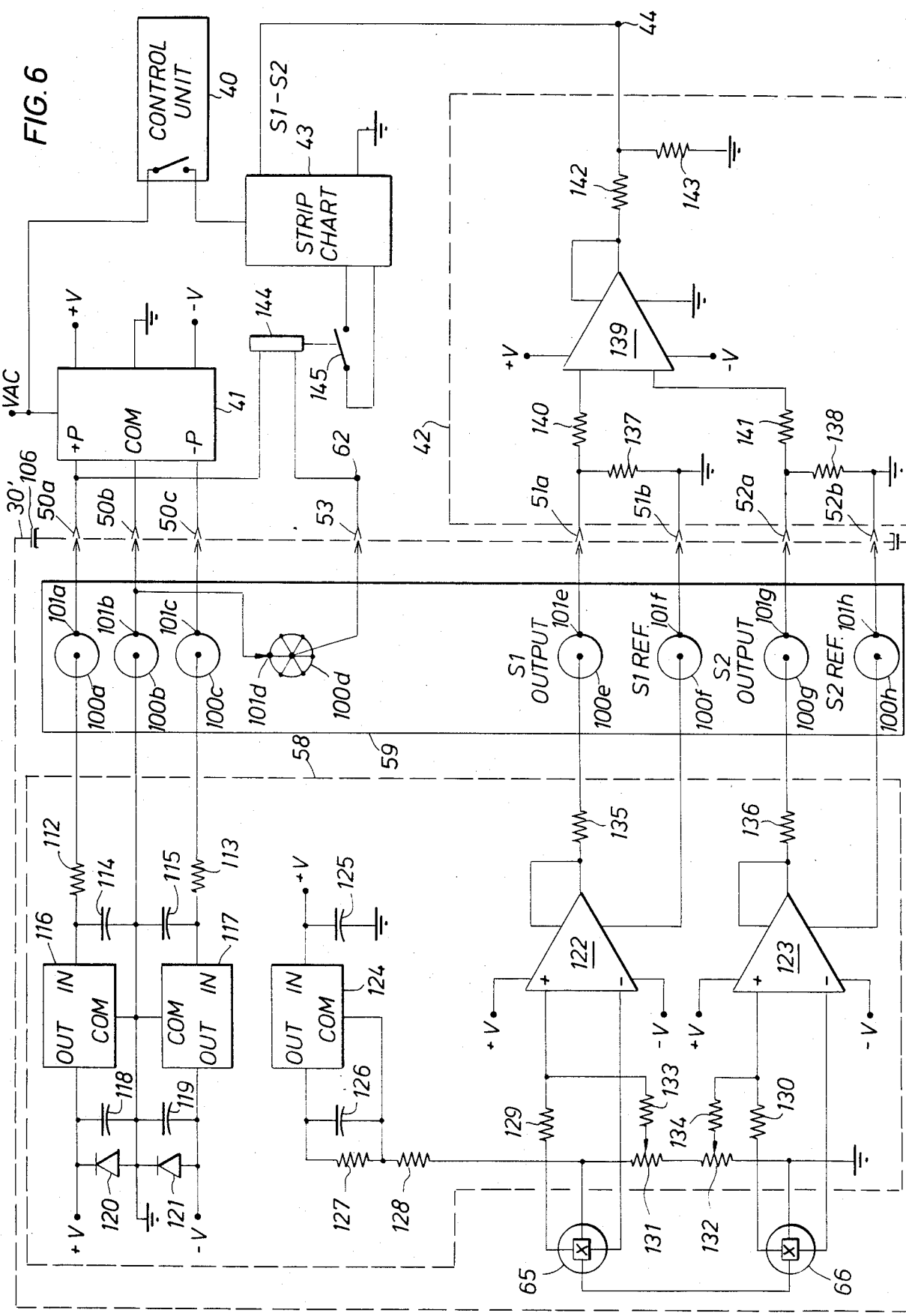
FIG. 6 is an electrical schematic of the amplifier, slip ring assembly and differential circuit of the system shown in FIG. 3 in accordance with the invention.

In FIG. 3, the signal power source 41 is shown as applying voltage (V) to the differential circuit 42 and as providing power (P) through the connector 50 to the sensing units 55 and 56 and the amplifier 58 via the slip ring assembly 59. Referring in more detail to FIG. 6, the signal power supply 41 provides regulated voltage (±V) to the differential amplifier circuit 42 and unregulated voltage (±P) to the brush assemblies 101a and 101c of the slip ring assembly 59 through connectors 50a and 50c in the grommet 106 of the head 30'. The slip rings 100a and 100c are each connected to resistors 112 and 113 which are each serially connected to capacitors 114 and 115, each of which is grounded in proper polarity to the common terminal of the signal power supply 41 through the brush assembly 101b and the slip ring 100b via connector 50b in the grommet 106 of the head 30'. The unregulated voltage (±P) is of sufficient magnitude to overcome the losses through the cable 36 (FIG. 2) extending between the truck 32 and the grommet 106 (FIG. 6) of the head 30'. A positive and a negative voltage regulator 116 and 117 are connected across the capacitors 114 and 115, respectively, and provide regulated voltage (±V) across output capacitors 118 and 119, respectively, in parallel combination with diodes 120 and 121, respectively, for differential amplifiers 122 and 123 and a voltage regulator 124. The output capacitors 118 and 119 are used to improve the transient response, while the capacitors 114 and 115 are used to filter the input to the voltage regulators 116 and 117 which can be, for example, types 78MG and 79MG respectively, manufactured by Fairchild.

The input of the voltage regulator 124, which can also be type 78MG, is filtered by a grounded capacitor 125. A capacitor 126 and a resistor 127 are connected in parallel across the output and common terminal of the voltage regulator 124 to provide a constant current source through a resistor 128 which provides a rated input control current ($I_c$) of approximately 200 mA to the serially connected Hall elements 65 and 66. An output terminal from each of the elements 65 and 66 is connected through resistors 129 and 130, respectively, to the noninverting terminals of the differential amplifiers 122 and 123, respectively; the other output terminal from each of the elements 65 and 66 is connected to the inverting terminal of the differential amplifiers 122 and 123. Differences in the offset voltage of the elements 65 and 66 are normalized by an offset adjustment network comprising variable resistors 131 and 132 serially connected across the serially connected Hall elements 65 and 66. The wipers of the variable resistors 131 and 132 are serially connected through resistors 133 and 134, respectively, to the noninverting terminals of the amplifiers 122 and 123, respectively, and can be separately adjusted to compensate for the offset differences. The amplifiers 122 and 123, which can be, for example, a type AD-521 manufactured by Analog Devices, also employ a gain trim adjustment network (not shown) to normalize the sensitivity of each channel. The gain of the amplifiers 122 and 123 is adjusted between approximately 60 and 200. The positive output, S1, from the amplifier 122 is serially connected through a resistor 135 to the slip ring 100e, and the reference output is connected to the slip ring 100f; the positive output, S2, from the amplifier 123 is serially connected through a resistor 136 to the slip ring 100g, and the reference output is connected to the slip ring 100h. The slip rings 100e through 100h transmit these signals via the corresponding brush assemblies 101e through 101h and connectors 51a, 51b, 52a and 52b, respectively, in the grommet 106 of the head 30'. The cable 36 (FIG. 2) routes these signals into the truck 32 where they are connected to the differential circuit 42 (FIG. 6).

The differential circuit 42 comprises resistors 137 and 138 which are serially connected between the resistors 135 and 136, respectively, and grounded to load the outputs of the amplifiers 122 and 123, respectively, so that the output voltage appears primarily across the resistors 137 and 138. The reference output from each amplifier 122 and 123 is also grounded. The differential circuit 42 also comprises a differential amplifier 139 having a noninverting terminal serially connected through a resistor 140 to the junction between resistors 135 and 137 and an inverting terminal serially connected through a resistor 141 to the junction between the resistors 136 and 138. The amplifier 139, which also can be a type AD-521 employing an output offset trim adjustment network (not shown), subtracts the amplified signals, S1 and S2, and applies the output (S1-S2) across resistors 142 and 143, the junction between which is connected through the terminal 44 to the strip chart 43. The gain of the amplifier 139 can be set to 1 or 10 by a switch (not shown) to scale the output reading on the strip chart 43.

The slip ring assembly 59 also comprises a slip ring 100d which supplies a momentary contact through the brush assembly 101d to the common terminal of the signal power supply 41 via the brush assembly 101b each time the slip ring 100d rotates through an angular displacement of approximately 60 degrees. The slip ring 100d is connected through the connector 53 in the grommet 106 of the head 30' and to the terminal 62. An input relay 144 associated with the strip chart 43 is connected to the terminal 62 and is energized by the signal power supply 41 (+P) each time the slip ring 100d momentarily completes the circuit through the brush assembly 101d. When the relay 144 is energized by the momentary contact signal (M), it actuates a switch 145 which provides a signal that is recorded on the strip chart 43 each time the slip ring 100d rotates 60 degrees. Since the rotation of the slip ring assaembly 59 is synchronized with the rotation of the elements 65 and 66, the signal from the switch 145 scales the differential output signal (S1-S2) for each 60 degrees of angular displacement. Consequently, when the differential output signal (S1-S2) indicates the existence of a flaw in the pin of a pipe, the flaw, which might not be readily visible, can be easily located by first counting the number of 60 degree increments recorded on the strip chart 43.

It is to be understood that a scale factor other than 60 degrees can be used to locate a flaw in the pin of a pipe.

Figure 7:
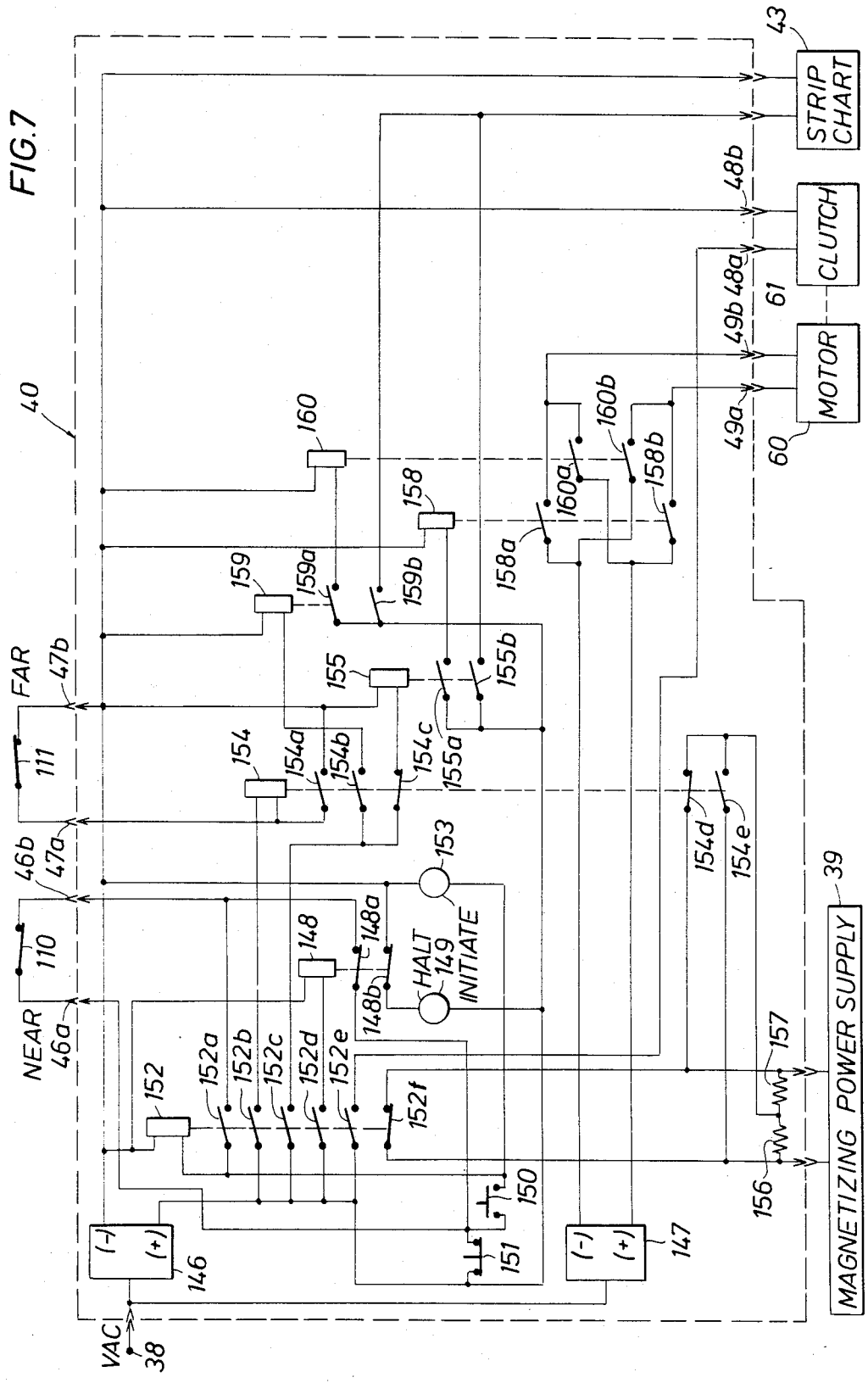
FIG. 7 is an electrical schematic of the control unit of the system shown in FIG. 3 in accordance with the invention.

Power is provided to the strip chart 43 through the control unit 40. Referring now in more detail to FIG. 7, the control unit 40 comprises two power supplies 146 and 147 provided with 115 VAC at the terminal 38 and other electronic components shown within the dashed line which is also indicated by the numeral 40. A time-delay relay 148 actuates two switches 148a and 148b from a normally-closed position to an open position when energized. In the deenergized state, the normally-closed switch 148b connects a HALT lamp 149 to the power supply 146 which illuminates the lamp 149. The inspection sequence is started when the operator 37 (not shown) depresses and closes a normally-open momentary contact switch 150 which is connected to the power supply 146 through a normally-closed momentary disconnect switch 151 and which in turn causes a latch relay 152 to be energized by the power supply 146. The relay 152 actuates switches 152a through 152e from a normally-open position to a closed position and switch 152f from a normally-closed position to an open position. The switch 152d connects the power supply 146 to the time-delay relay 148 which does not actuate the switches 148a and 148b for a period of approximately 2.5 seconds after being energized. Therefore, the latching switch 152a, which connects the junction between the two momentary switches 150 and 151 through the closed switch 148a to the relay 152, will keep the relay 152 energized after the momentary contact switch 150 is released. The latching switch 152a also connects an INITIATE lamp 153 to the power supply which illuminates the lamp 153. The switch 152b connects the power supply 146 to a relay 154 having three normally-open switches 154a, 154b and 154e and two normally closed switches 154c and 154d. The power supply 146 does not energize the relay 154 until the normally-open FAR limit switch 111 is closed. Consequently, the switch 152c connects the power supply 146 to a time-delay relay 155 which after approximately 2.0 seconds actuates switches 155a and 155b from a normally-open position to a closed position.

The switch 152e connects the clutch 61 to the power supply 146 through the cable 36 (not shown) and the connectors 48a and 48b of the head 30' causing the clutch to engage the motor 60 to the spur gear 86 (not shown); the motor 60 itself has not yet been energized. The current supplied to the solenoid 68 (not shown) by the magnetizing power supply 39 can be set at a high value or a low value depending on which of two serially connected resistors 156 and 157 is shorted. The open switch 152f connected in parallel with the resistors 156 and 157 allows the normally closed switch 154d to short the LOW FIELD resistor 157, so that the HIGH FIELD resistor 156 sets the magnetizing power supply 39 to provide enough current to the solenoid 68 (not shown) to magnetically saturate the pin 21 (not shown). Thus, just before two seconds has elapsed, the HALT and INITIATE lamps 149 and 153, respectively, are illuminated and the solenoid 68 (not shown) and the clutch 61 are energized. When the relay 155 actuates the switches 155a and 155b after approximately two seconds has elapsed, the motor 60 and the strip chart 43 are simultaneously activated to commence a forward scan cycle. The switches 155b and 155a connect the power supply 146 to the strip chart 43 and a relay 158, respectively. The relay 158 actuates switches 158a and 158b from a normally-open position to a closed position so that the power supply 147 is connected to the motor 60 through the cable 36 (not shown) and the connectors 49a and 49b of the head 30'. When the motor 60 starts rotating the cylindrical tube 91 (FIG. 5), the cam 108 supported thereon rotates away from and releases the actuating roller 110a of the NEAR limit switch 110 to return it to the normally-closed position. The NEAR limit switch 110 connects the junction between the two momentary switches 150 and 151 (FIG. 7) to the latch switch 152a through the cable 36 (not shown) and the connectors 46a and 46b in the grommet 106 of the head 30' so that the relay 152 and the INITIATE lamp 153 remain energized when the time-delay relay 148 after approximately 2.5 seconds actuates the switch 148a from the normally-closed position to the open position. The relay 148 also opens the switch 148b which disconnects the HALT lamp 149 providing an indication to the operator 37 (not shown) that the forward scan cycle is in progress.

After the cylindrical tube 91 (FIG. 5) has rotated and traversed the full length of the forward scan of the pin 21, the cam 108 supported thereon rotates under the roller 111a of the FAR limit switch 111 which is actuated from a normally-open position to a closed position. The FAR LIMIT switch 111 (FIG. 7) connects the relay 154 to ground through the cable 36 (not shown) and connectors 47a and 47b in the grommet 106 of the hand 30', so that the relay 154 is energized by the power supply 146 through the switch 152b. As a result, the switch 154c opens and causes the relay 155 to deenergize which in turn causes the motor 60 and the strip chart 43 to shut down, marking the end of the forward scan cycle. The switch 154d opens and the switch 154e closes to short out the HIGH FIELD resistor 156. Thus, the LOW FIELD resistor 157 sets the magnetizing power supply 39 to reduce the amount of current in the solenoid 68 (not shown) to a value near zero, so that the magnetic field in the pin 21 (not shown) decreases to its residual value. The switch 154b energizes a time-delay relay 159 which after approximately ten seconds actuates switches 159a and 159b from a normally-open position to a closed position. After the ten-second period of inactivity during which the operator 37 (not shown) readjusts the scaling of the strip chart 43, the activated switches 159b and 159a cause the strip chart 43 and the motor 60 to be simultaneously reactivated so that the motor 60 rotates in the reverse direction to commence a reverse scan cycle. The switches 159b and 159a connected the power supply 146 to the strip chart 43 and a relay 160, respectively. The relay 160 actuates switches 160a and 160b from a normally-open position to a closed position so that the power supply 147 is connected to the motor 60, but in reverse polarity. Consequently, the motor rotates the cylindrical tube 91 (FIG. 5) in the reverse direction so that the cam 108 releases the actuating roller 111a of the FAR limit switch 111 to return it to the normally-open position. Even though the FAR limit switch 111 (FIG. 7) is opened, the relay 154 remains energized because the latching switch 154a provides a path to ground.

When the reverse scan cycle is completed, the cam 108 (FIG. 5) rotates under and actuates the roller 110a of the NEAR limit switch 110 which opens and causes the relay 152 (FIG. 7) to be deenergized and the INITIATE lamp 153 to be extinguished. Consequently, the motor 60, the clutch 61 and the strip chart 43 are deactivated and the HALT lamp again illuminated to indicate that scanning has been completed and that the control unit 40 is at the same state as it was before the momentary contact switch 150 was first depressed by the operator 37 (not shown). The scanning sequence can be terminated at any time by depressing the momentary disconnect switch 151, at which time the HALT lamp 149 is illuminated. Scanning is reinitiated by depressing the momentary contact switch 150.

Figure 8:
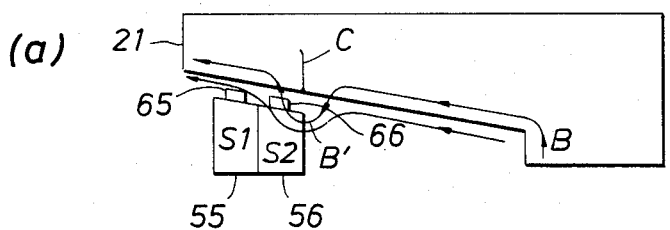
FIG. 8 is a schematic, vertical sectional view of the magnetic sensing means of FIG. 4 shown in operation and a graph showing the resultant output signals therefrom.
Figure 8:
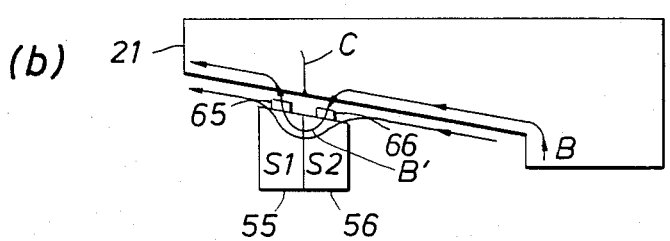
Figure 8:
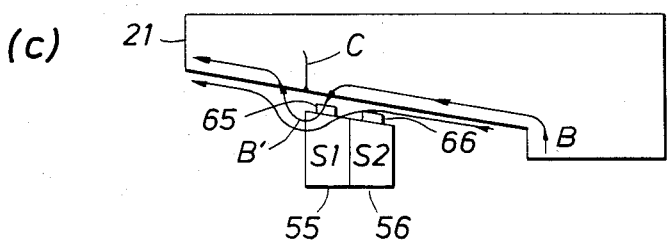
Figure 8:
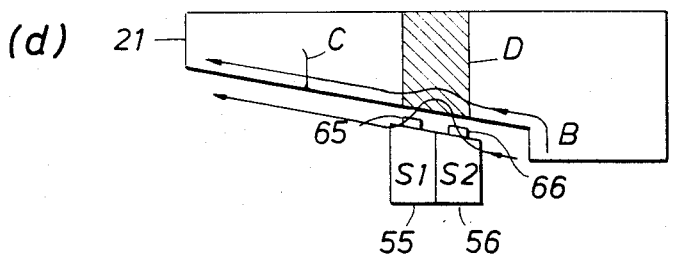
Figure 8:
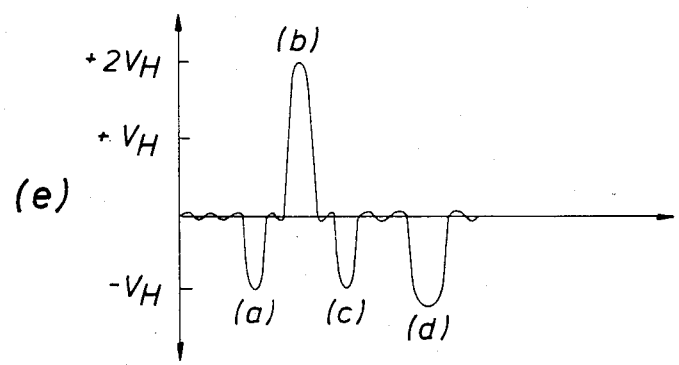

During the forward scan cycle, the magnetizing circuit 54 (FIGS. 3 and 5) generates magnetic flux through the pin 21 along the path approximated by the dashed lines 81 and 82. The current through the solenoid 68 is set sufficiently high by the magnetizing power supply 39, so that the flux 81 and 82 is of sufficient magnitude to magnetically saturate the pin 21. Saturation is required to detect small flaws such as, for example, the crack indicated at C in FIGS. 8(a) through 8(c). The flow of magnetic flux through the pin 21 can be evaluated by observing the path of field lines approximated by the paths B which are diverted by the crack C. The crack C creates a discontinuity in the permeability of the pin 21 which causes a perturbation B' in the field lines B having a normal component pointing into the pin 21 (positive direction) on one side of the crack C and a normal component pointing out from the pin 21 (negative direction) on the other side of the crack C. Referring back to FIG. 4, the elements 65 and 66 produce an output voltage ($V_H$) proportional to the product of the control current ($I_C$) and the component of magnetic flux (B) perpendicular to the surface of the elements 65 and 66. Therefore, when the sensing units 55 and 56 begin the forward scan toward the crack C as shown in FIG. 8(a), the positive normal component of the perturbation B' causes a positive potential, $V_H$, to develop across the element 66 of the second sensing unit (S2) 56, while no voltage develops across the element 65 of the first sensing unit (S1) 55. As a result, the differential output signal, S1-S2, is equal to a negative voltage, $-V_H$, as graphically illustrated at (a) in FIG. 8(e). After sensing units 55 and 56 rotate a full revolution to the position directly over the crack C as shown in FIG. 8(b), the positive normal component of the perturbation B' causes a positive potential, $V_H$, to develop across the element 65 of the first sensing unit (S1) 55, while the negative normal component causes a negative potential, $-V_H$, across the element 66 of the second sensing unit (S2) 56. In this case the differential output, S1-S2, is equal to twice the positive voltage, $2V_H$, as graphically illustrated at (b) in FIG. 8(e). After another revolution away from the crack C shown in FIG. 8(c), the negative normal component of the perturbation B' causes a negative potential, $-V_H$, to develop across the element 65 of the first sensing unit (S1) 55, while no voltage develops across the element 66 of the second sensing unit (S2) 56. Thus, the differential output, S1-S2, is again equal to a negative voltage, $-V_H$, as graphically illustrated at (c) in FIG. 8(e). The composite graph of (a), (b) and (c) represents a signature identifying the crack C as a flaw in the pin 21.

Other discontinuities and irregularities such as gouges and dents will produce a signature similar to that produced by the crack C. However, if the flaw in the pin 21 is a plastic deformation caused by subjecting it to excessive tension or compression as indicated at D in FIG. 8(d), the deformation causes a local change in permeability which can be detected during the reverse scan cycle when the solenoid 68 (FIG. 5) is deenergized. When the magnetic field 81 and 82 saturates the pin 21 and is subsequently removed, the field through the pin 21 collapses to different residual values for the deformed (D in FIG. 8(d)) and nondeformed portions. It has been discovered that although the deformation D remains unidentified during the forward scan cycle, it is identifiable during the reverse scan cycle by a signature similar to that illustrated graphically at (d) in FIG. 8(e). Thus, significant and detectable signatures are obtained from plastic deformations with or without associated cracks in the pin 21 as well as from very small fatigue cracks.

Referring in more detail to FIG. 9, a head for inspecting the box 23 is indicated generally at 30″ and represents the embodiment of the head 30 (FIG. 3) described above as represented by similar numerals where appropriate. The head 30″ comprises a first tubular housing 161 having a flange 162 on one end directed radially inwardly, a solenoid 163 positioned longitudinally within the housing 161, a second tubular housing 164 having a closed end 165 and having a flange 166 on the other end directed radially outwardly and bolted to the flange 162 of the first housing 161, and an annulus 167 closing the other end of the first housing 161 and having an inner diameter sufficiently large to receive the box 23 which moves toward the exposed inner surface of flange 162 when inserted into the head 30″ through the orifice of the outer annulus 167. The head 30″ also comprises a support tube 168 having one end mounted by a rolling-contact bearing 169 in the closed end 165 of the second housing 164 and extending therethrough to a handle 170, a flange 171 extending radially therefrom and rotatably mounted by a rolling-contact bearing 172 within the flange 166 of the second housing 164, and the other end threaded to have a pitch equal to the horizontal component of the pitch of the box 23. One end of a tubular screw 173 is attached to the mounting flange 171 of the support tube 168. When the box 23 is inserted into the head 30″ through the orifice of the receiving annulus 167, it is threadably engaged by the tubular screw 173 as the handle 170 is rotated so that the end of the box 23 moves toward the exposed inner flange 162 of the first tubular housing 161. The magnetizing circuit 54 (FIG. 3) comprises the outer annulus 167 (FIG. 9), the first housing 161 and its flange 162, which are all ferromagnetic, as well as the box 23 itself. The solenoid 163 is connected to the magnetizing power supply 39 (FIG. 3) and, when energized thereby, gives rise to a magnetic flux through the ferromagnetic elements of the magnetizing circuit 54 and the box 23 (FIG. 9) along a doughnut-shape path approximated in cross section by dashed lines 174 and 175.

The motor 60 is mounted on the flange 171 of the support tube 168 and direct drives the clutch 61 by a shaft 176. When the clutch 61 is enabled, it engages a drive shaft 177 the other end of which is rotatably mounted by a rolling-contact bearing 178 on a bracket 179 attached to the support tube 168. An elongated spur gear 180 is housed within the support tube 168 on a shaft 181 rotatably mounted at each end by journal bearings 182 and 183, and engaged through an opening 184 in the support tube 168 by a gear wheel 185 mounted on the drive shaft 177. The end of the shaft 181 extending through the bearing 183 is attached to the inside base of a cup 186, the inside walls of which threadably engage the threaded end of the support tube 168. A nonmagnetic shell 187 having the shape of a conical frustum which corresponds to the taper of the box 23 and the inner diameter of its crests, is attached at its base to the tubular screw 173 and tapers to a closed end rounded to seat within the box 23. When the box 23 is inserted into the head 30" to threadably engage the tubular screw 173, the handle 170 is rotated until the threads inside the box 23 seat against the outside surface of the shell 187. The bracket 57 for the sensing units 55 and 56 is mounted on a piston assembly 188 extending radially outwardly from the outside wall of the rotating cup 186. The piston assembly 188 is contained within a helical spring 189 disposed between the cup 186 and the bracket 57 so that the sensing units 55 and 56 are urged against the inside surface of the shell 187. As the gear wheel 185 rotates and causes the cup 186 to turn, the sensing units 55 and 56 follow the helical path defined by the threads of the box 23 with the shell 187 disposed therebetween, while the spur 180 and the shaft 181 slide axially within the support tube 168. The sensing units 55 and 56 and shell 187 are configured as described above with respect to the head 30' (FIG. 5).

The amplifier 58 (See also FIG. 9) is mounted on a circuit board 190 attached to the outside walls of the rotating cup 186. The slip ring assembly, indicated generally at 59, is similar in construction to that described above with respect to the head 30'. However, in this embodiment the brush assemblies 101a through 101d are not mounted on a bracket, but rotate synchronously with the amplifier 58, while the slip rings 100a through 100d are stationary with respect to the support tube 168 on which they are mounted. The brush assemblies 101a through 101d are mounted on a bracket 191 which is supported by the table 192 of a slide bearing extending radially inwardly from its bed 193 within the tubular screw 173. The table 192 rides in the bed 193 which extends the full circumference of the tubular screw 173. A cylinder 194 is attached to the bracket 191 and houses a piston 195 which extends axially from the rim of the cup 186 to which it is attached. Thus, as the cup 186 is turned by the shaft 181, the piston 195 causes the brush assemblies 101a through 101d to rotate in electrical contact with the slip rings 100a through 100d, and slides out of the cylinder as the cup 186 rotates away from the assembly 59. Although only four slip rings 100a through 100d are shown, an additional four 100e through 100h not shown are used in operation along with corresponding brush assemblies 101a through 101h. The amplifier 58 is electrically connected (not shown) through the slip ring assembly 59 to another slip ring assembly, indicated generally at 196, through a hole 197 in the flange 171. Power for the motor 60 and the clutch 61, the power ($\pm$P) to and the signals (S1 and S2) from the amplifier 58, and the momentary contact signal (M) are transmitted through the slip rings 198 and the corresponding stationary brush assemblies 199 out of the head 30" via a connector 200 in the tubular shell 164. Although only three slip rings 198 are shown, additional ones not shown are used in combination with additional brush assemblies 199 in operation to accommodate the above-mentioned signals.

The NEAR limit switch 110 is mounted on the inside surface of the tubular screw 173 and the FAR limit switch 111 is mounted on the inside surface of the shell 187. An arm 201 extending axially from the rim of the cup 186 toward the flange 171 supports a cam 202 which rotates away from and releases the actuating roller 110a of the NEAR limit switch 110 when the motor 60 starts rotating the cup 186. After the cup 186 has rotated to the end of the helical path, the cam 202 rotates under the roller 111a of the FAR limit switch 111 which is actuated thereby. Both switches 110 and 111 are electrically connected outside the head 30" through the hole 197 in the flange 171 and the slip ring assembly 196 via the connector 200. The solenoid 163 is also electrically connected outside the head 30" through the connector 200 and forms, along with the other connections therethrough, the cable 36 to the truck 32 (FIG. 2). The amplifier 58 (FIG. 6), slip ring assembly 59, differential circuit 42 and the control unit 40 (FIG. 7) are constructed and operated as described hereinabove with respect to the embodiment of the head 30' for inspecting the pin 21 of the pipe 22.

The instant method for detecting flaws in the pin 21 of the pipe 22 or the box 23 of the pipe 24 involves several steps. The threaded end is first internalized by the head 30 (FIG. 3) to become part of the magnetizing circuit 54. Referring to FIG. 5, when the pin 21 of the pipe 22 is inserted into the head 30', it is piloted through the orifice of the annulus 71 by the guide 76 and threadably engaged by the tubular screw 80 as the handle 79 is rotated so that the threads 26 of the pin 21 seat against the conical shell 92. Referring to FIG. 9, when the box 23 is inserted into the head 30" in a corresponding fashion, it is threadably engaged by the tubular screw 173 as the handle 170 is rotated so that the threads of the box 23 seat against the shell 187. The control unit 40 (FIG. 3) then causes a magnetic force (81 and 82 in FIG. 5 and 174 and 175 in FIG. 9) to be applied whereupon the magnetic force produces a field generally axially through the threaded end during the forward scan as described hereinabove with respect to FIG. 7. Consequently, the sensing units 56 and 57 generate the signals S1 and S2 which correspond to the sensed magnetic fields described hereinabove with respect to FIGS. 8a through c, and which are amplified, differentially connected, and recorded as described in FIG. 6 to produce an output signal or signature shown in FIG. 8e whenever a flaw is detected. The control unit 40 (FIGS. 3 and 7) finally cause the magnetic force to be removed whereby the field in the threaded end of the pipe decreases to its residual value during the reverse scan as described hereinabove. Consequently, the sensing units 56 and 57 generate the signals S1 and S2 to produce a differential output signal or signature as described hereinabove with respect to FIGS. 8d and 8e whenever a deformation is detected.

It will be apparent that various changes may be made in details of construction from those shown in the attached drawings and discussed in conjunction therewith without departing from the spirit and scope of this invention as defined in the appended claims. For example, the apparatus and method can be used to detect flaws in any piece of threaded pipe regardless of the specific application. It is, therefore, to be understood that this invention is not to be limited to the specific details shown and described.

What we claim is:

1. Apparatus for detecting flaws in the threaded end of an elongate member, comprising:
    an electromagnetic means for applying a magnetic force in a direction substantially parallel with the longitudinal axis of said elongate member so as to generate a magnetic field in said threaded end;
    at least two axially-spaced sensing means for detecting deviations in the magnetic field from said axial direction and for generating first and second signals corresponding to said deviated magnetic field at selected axially separated positions relative to said threaded end wherein each said sensing means is radially aligned in spaced relationship with respect to the surface of the crests of the thread of said threaded end;

means for effecting relative rotational movement between said sensing means and said threaded end wherein said rotational means includes:
- a first support means having a helical-shaped portion,
- a second support means having said sensing means attached thereto and having a helical-shaped portion wherein said helical-shaped portion of said first support means and said helical-shaped portion of said second support means are in helical rotational engagement,
- means for attaching said threaded end to said first support means, and
- drive means for revolving said second support means relative to said first support means so that each said selected positions follows a helical path substantially similar to the crests of the thread of said threaded end; and means responsive to said first and second signals for generating an output signal related to the difference between said first and second signals to provide an indication of a flaw in the threaded end.

2. Apparatus as recited in claim 1, wherein said magnetic field is in one generally axial direction, and which apparatus further comprises means for terminating the application of said magnetic force by said electromagnetic means, resulting in the reduction of said magnetic field to a residual value wherein said output signal from said responsive means continues to provide an indication of a flaw in the threaded end.

3. Apparatus as recited in claim 1, which further comprises a shell disposed between said sensing means and the crests of said threaded end for mechanically isolating said sensing means from the crests of said threaded end without substantially attenuating said magnetic field at said selected positions.

4. Apparatus as recited in claim 3, wherein said shell is a nonmagnetic material.

5. Apparatus as recited in claim 4, wherein the nonmagnetic material is brass.

6. Apparatus as recited in claim 4, wherein the nonmagnetic material is beryllium copper.

7. Apparatus as recited in claim 1, wherein said sensing means are proximate the surfaces of successive crests of the thread of said threaded end.

8. Apparatus as recited in claim 1, wherein each said sensing means includes a Hall element, each having a sensing surface aligned on a plane substantially parallel to the crests of the thread of said threaded end.

9. Apparatus for detecting flaws in the threaded end of an elongate member, comprising:
- means for applying a magnetic force so as to generate a magnetic field in one generally axial direction through said threaded end;
- means for sensing deviations in the magnetic field from said axial direction and for generating first and second signals corresponding to said deviated magnetic field at selected axially separated positions relative to said threaded end;
- means for effecting relative rotational movement between said sensing and generating means and said threaded end wherein said rotational means includes:
  - a first support means having a helical-shaped portion,
  - a second support means having said sensing means attached thereto and having a helical-shaped portion wherein said helical-shaped portion of said first support means and said helical-shaped portion of said second support means are in helical rotational engagement,
  - means for attaching said threaded end to said first support means, and
  - drive means for revolving said second support means relative to said first support means so that each said selected positions follows a helical path substantially similar to the crests of the thread of said threaded end;
- means responsive to said first and second signals for generating an output signal related to the difference between said first and second signals to provide an indication of a flaw in the threaded end; and
- means for terminating the application of said magnetic force by said applying means, resulting in the reduction of said magnetic field to a residual value wherein said output signal from said responsive means continues to provide an indication of a flaw in the threaded end.

10. Apparatus as recited in claim 9, which further comprises a shell disposed between said sensing means and the crests of said threaded end for mechanically isolating said sensing means from the crests of said threaded end without substantially attenuating said magnetic field at said selected positions.

11. Apparatus as recited in claim 10, wherein said shell is a nonmagnetic material.

12. Apparatus as recited in claim 11, wherein the nonmagnetic material is brass.

13. Apparatus as recited in claim 11, wherein the nonmagnetic material is beryllium copper.

14. Apparatus as recited in claim 9, wherein said sensing means includes at least two sensors located adjacent successive crests of the thread of said threaded end.

15. Apparatus as recited in claim 9, wherein said sensing means includes at least two Hall elements each having a sensing surface aligned on a plane substantially parallel to the crests of the thread of said threaded end.

16. Apparatus for detecting flaws in the threaded end of an elongate member, comprising:
- an electromagnetic means for applying a magnetic force in a direction substantially parallel with the longitudinal axis of said elongate member so as to generate a magnetic field in said threaded end;
- at least two axially-spacing sensing means for detecting deviations in the magnetic field from said axial direction and for generating first and second signals corresponding to said deviated magnetic field at selected axially separated positions relative to said threaded end wherein each said sensing means is radially aligned in spaced relationship with respect to the surface of the crests of the thread of said threaded end;
- means for effecting relative rotational movement between said sensing means and said threaded end wherein said rotational means includes:
  - tubular screw support means having inner and outer threads, wherein said inner thread engages said threaded end,
  - a cylindrical cup having an inner thread to engage said outer thread of said screw support means, said cup supporting said sensing means, and drive means in spaced relationship to said screw support means so as to prohibit movement of said drive means relative to the transverse axis of said elongate member, said drive means having means for engaging said cup so that said cup rotates relative to said tubular screw support means so that each said selected positions follows a helical path substantially similar to the crests of the thread of said threaded end; and means responsive to said first and second signals for generating an output signal related to the difference between said first and second signals to provide an indication of a flaw in the threaded end.

17. Apparatus for detecting flaws in the threaded end of an elongate member, comprising:

an electromagnetic means for applying a magnetic force in a direction substantially parallel with the longitudinal axis of said elongate member so as to generate a magnetic field in said threaded end;

at least two axially-spaced sensing means for detecting deviations in the magnetic field from said axial direction and for generating first and second signals corresponding to said deviated magnetic field at selected axially separated positions relative to said threaded end wherein each said sensing means is radially aligned in spaced relationship with respect to the surface of the crests of the thread of said threaded end;

means for effecting relative rotational movement between said sensing means and said threaded end wherein said rotational means includes:

tubular screw support means having an outer thread to engage said threaded end, a cylindrical cup positioned in spaced relationship to said screw support means, said cup supporting said sensing means, and drive means engaging said cup so that said cup rotates relative to said screw support means so that each said selected positions follows a helical path substantially similar to the crests of the thread of said threaded end; and means responsive to said first and second signals for generating an output signal related to the difference between said first and second signals to provide an indication of a flaw in the threaded end.

18. Apparatus as recited in claim 16 or 17, which further comprises a shell disposed between said sensing means and the crests of said threaded end for mechanically isolating said sensing means from the crests of said threaded end without substantially attenuating said magnetic force at said selected positions.

19. Apparatus as recited in claim 18, wherein said shell is a nonmagnetic material.

20. Apparatus as recited in claim 19, wherein the nonmagnetic material is brass.

21. Apparatus as recited in claim 19, wherein the nonmagnetic material is beryllium copper.

22. Apparatus as recited in claim 16 or 17, wherein said sensing means includes at least two sensors located adjacent successive crests of the thread of said threaded end.

23. Apparatus as recited in claim 16 or 17, wherein said sensing means includes at least two Hall elements each having a sensing surface aligned on a plane substantially parallel to the crests of the thread of said threaded end.

24. A method for detecting flaws in the threaded end of an elongate member, comprising the steps of:

applying a magnetic force in a direction substantially parallel with the longitudinal axis of said elongate member so as to generate a magnetic field in the threaded end of the elongate member;

sensing deviations in said magnetic field from said axial direction at at least two selected axially separated positions relative to said threaded end with sensing means wherein said sensing of deviations occurs in radial alignment with respect to the surface of the crests of the thread of the threaded end;

generating first and second signals corresponding to said deviated magnetic field at said selected positions;

effecting the relative rotational movement of a first support means having a helical-shaped portion and a second support means having a helical-shaped portion wherein said helical-shaped portion of said first support means and said helical-shaped portion of said second support means are in helical rotational engagement and said first support means is attached to said threaded end and said sensing means is attached to said second support means so that each said selected positions follows a helical path substantially similar to the crests of the thread of said threaded end; and comparing said first and second signals so that a difference between said first and second signals is an indication of a flaw in the threaded end.

25. A method for detecting flaws in the threaded end of an elongate member comprising the steps of:

applying a magnetic force so as to generate a magnetic field generally axially through the threaded end of the elongate member;

sensing the generally radial magnetic field from at least two selected positions of a thread;

generating first and second signals corresponding to sensed portions of the magnetic field at said selected positions;

comparing said first and second signals whereby a difference between said first and second signals is an indication of a flaw in the threaded end;

removing said magnetic force, whereby said field decreases to a residual value;

sensing the generally radial residual magnetic field from at least two selected positions of a thread;

generating first and second signals corresponding to sensed portions of the residual magnetic field at said selected positions; and comparing said first and second signals whereby a difference between said first and second signals is an indication of a flaw in said threaded end.

26. A method as recited in claim 25, which further comprises the step of sensing the radial magnetic field along a portion of the length of a helical path corresponding to the thread of the elongate member, whereby the signals corresponding to the sensed portion of the residual magnetic field vary with time.

* * * * *